US00PP11601P

United States Patent [19]

Fischer et al.

[11] Patent Number: Plant 11,601

[45] Date of Patent: Oct. 24, 2000

[54] APPLE TREE NAMED 'PINOVA'

[76] Inventors: Hermann Manfred Fischer, Genbank Obst Dresden-Pillnitz am Institut für Pflanzengenetik und Kulturpflanzenforschung, Gatersleben Bergweg 23, D-01326 Dresden, Germany; Johann Schmadlak, Sobrigener Str. 3 b, D-01326 Dresden, Germany; Christa Martha Fischer, BAZ Quedlinberg Institut für Obstzüchtung Dresden-Pillnitz Pillnitzer Platz 2, D-01326 Dresden, Germany

[21] Appl. No.: 09/003,093

[22] Filed: Jan. 6, 1998

[51] Int. Cl.[7] ..... A01H 5/00

[52] U.S. Cl. ..... Plt./161

[58] Field of Search ..... Plt./161, 172

[56] References Cited

U.S. PATENT DOCUMENTS

P.P. 6,588 2/1989 Hauenstein ..... Plt./161
P.P. 10,739 12/1998 Lapins et al. ..... Plt./161

OTHER PUBLICATIONS

UPOV–ROM GTITM Computer Database 1999/02, GTI JOUVE Retrieval Software, citations for 'Pinova' Mar. 1999.

Bailey, Liberty Hyde, Ethel Zoe Bailey and Staff, Hortus Third Mac Millan, New York, pp. 699–701, 1976.

*Primary Examiner*—Howard J. Locker
*Assistant Examiner*—Wendy A Baker
*Attorney, Agent, or Firm*—Klarquist Sparkman Campbell Leigh & Whinson LLP

[57] ABSTRACT

A new and distinct variety of apple tree named 'Pinova' is provided. 'Pinova' is a dwarf apple variety that withstands both winter and spring frosts (i.e., a winter cultivar), with fruit of dessert quality with a smooth skin finish (little or no russeting), displays higher productivity on average than 'Golden Delicious' and no alternate bearing, and has less storage loss than 'Golden Delicious'. 'Pinova' is a high-quality cultivar that complements 'Golden Delicious' in the market until June.

4 Drawing Sheets

BACKGROUND OF THE INVENTION

The present invention comprises a new and distinct variety of apple tree, referred to by the varietal name 'Pinova'. The original tree of the new variety was the result of a cross between 'Clivia' and 'Golden Delicious' and was discovered in a cultivated area in Dresden-Pillnitz, Germany.

This invention has not been observed under all possible environmental conditions. However, the following combination of traits have been repeatedly observed in asexually propagated progeny and in combination distinguish 'Pinova' as a new and distinct apple variety: (1) a dwarf variety; (2) withstands both winter and spring frosts (i.e., a winter cultivar); (3) fruit of dessert quality with a smooth skin finish (little or no russeting); (4) higher productivity on average than 'Golden Delicious'; (5) no alternate bearing; (6) and less storage loss than 'Golden Delicious'. 'Pinova' is a high-quality cultivar that complements 'Golden Delicious' in the market until June.

BRIEF DESCRIPTION OF THE DRAWINGS

The following drawings are photographs of 'Pinova' taken at the Fruit Research Institute, Dresden-Pillnitz, Germany.

DETAILED DESCRIPTION OF THE INVENTION

Figure 1:
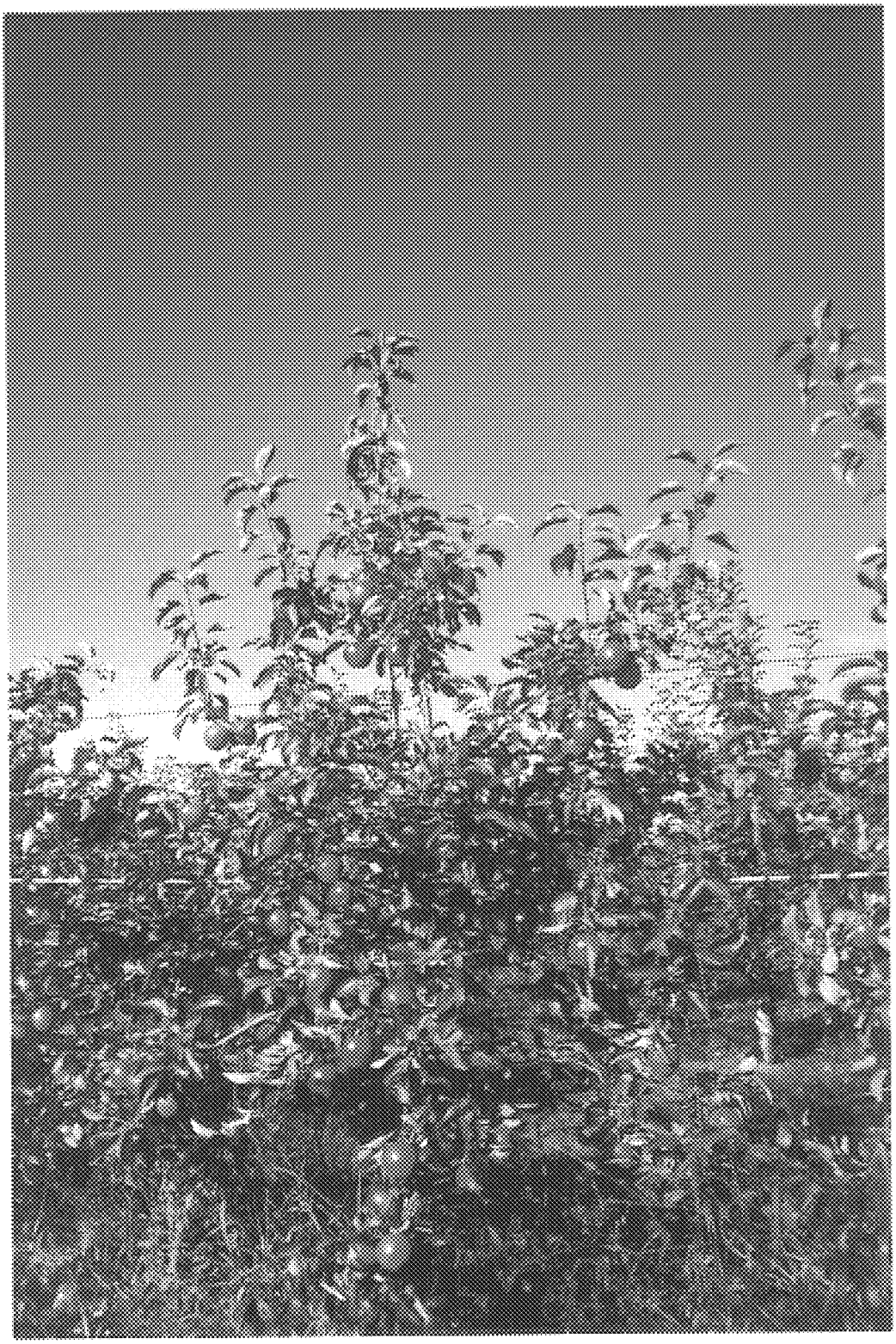
FIG. 1 is a view of a tree of the variety 'Pinova'.
Figure 2:
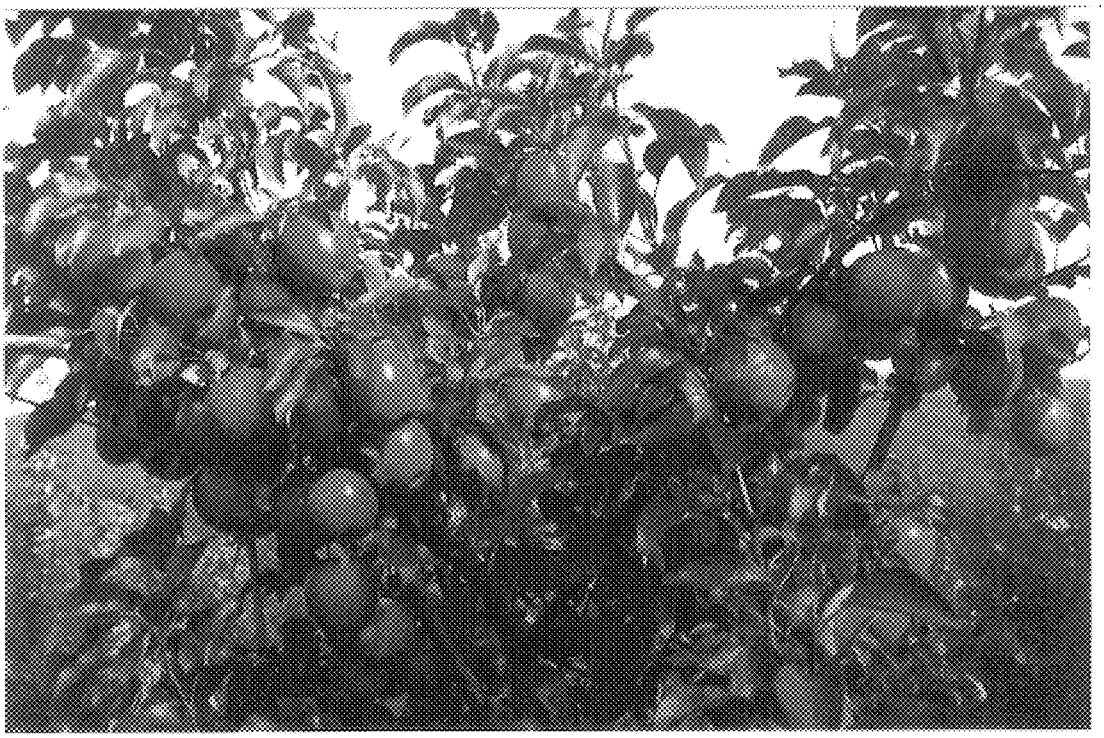
FIG. 2 is a close-up view of a branch of the variety.

The following is a detailed description of the invention based on plants that were grown in Dresden-Pillnitz, Germany and observed at that location between 1986 and 1996, unless otherwise indicated. All trees were of croppinjg maturity. For comparison purposes, except as noted below, fruit from all the strains as noted were grown at Dresden-Pillnitz, Germany, and were from trees of similar age.

Color descriptions and other terminology are used herein in accordance with ordinary dictionary significance or as commonly used by those of ordinary skill in the relevant art, unless otherwise noted. Color varies significantly with growing conditions and locations. For example, the fruit has been observed to be more orange in color when grown in hotter growing conditions, and more red in color when grown under cooler conditions. Soil conditions, such as the amount of nitrogen in the soil, affects fruit color and also leaf color. Colors are also affected by the amount of sunlight received by the fruit as the fruit matures, with fruit growing in shaded areas inside of a tree having less red color.

All trees of 'Pinova', insofar as I have been able to observe them, have been identical in all the characteristics described below.

Species: *Malus domestica* Borkh.

Parentage: 'Clivia' ('Duchess of Oldenburg'×'Cox's Orange Pippin')×'Golden Delicious'. All of which are believed to be unpatented.

Propagation: Holds to distinguishing characteristics through succeeding asexual propagations by budding and grafting.

Locality where grown and observed: Dresden-Pillnitz, Germany (except as otherwise noted).

Dates of first and last picking: Ready for harvest in the second and third weeks of October in Dresden-Pillnitz, Germany.

Tree:

*Size.*—Small to medium.

*Vigor.*—Dwarf. Trees growing in Dundee, Ore. observed early in summer during one growing season had internode lengths of about 25 to 33 mm. Vigor comparable to 'Braeburn' (unpatented). The variety is very precocious and early fruiting will reduce vigor.

*Growth rate.*—Medium to low.

*Habit.*—Upright, good ramification, broad.

*Pruning.*—Similar to 'Golden Delicious'. Requires regular renewal of fruiting branches and shoots. Does well as a slender spindle. High flower numbers preferably reduced by regular pruning and fruit thinning.

*Trunk.*—Straight, smooth. Bark color of three-year old trunk bark growing in Dundee, Ore., reddish brown, like R.H.S. 166B.

*Branches.*—Normal to thin, angle about 60° with respect to trunk. One year old shoots: medium.

*Lenticels.*—Many. Size: Large to very large. Color: Pale brown.

Leaves:

*Size.*—Medium to large. In one observation in Dundee, Ore. in early summer, several measured typical leaves were 80 to 90 mm. long (without the petiole which itself ranged from 18 to 28 mm. on these leaves) and 50 to 62 mm. wide.

*Shape.*—Ovate, serrate margin.

*Petiole.*—Medium.

*Color.*—Green to pale green. Varies with growing conditions. Leaves observed in early summer in one growing season in Dundee, Ore. had an upper leaf surface color like R.H.S. 143A and a lower leaf surface color like R.H.S. 143C.

Flower: Blooms regularly and abundantly. Full blooming each year.

*Size.*—Medium (to large). Typical open flower diameter in one observation in Wenatchee, Wash., was 48 mm. Closed flower diameter in the observation at this location typical being 8 mm. in diameter and 6 mm. in length.

*Color.*—Red-Purple to pink-white. Open flower, white, like R.H.S. 155B, with red-purple to pink, like R.H.S. 56C to 57D included therein.

*Petals.*—Five.

*Pistil.*—Stigma — bulbous on top; anthers — 13 to 15 in a single row, pale yellow, like R.H.S. 9C.

*Fragrance.*—Very slight.

*Flowering period.*—Mid-season (with 'Golden Delicious' and 'Gloster'). Bloom time comparable to 'Gala' (unpatented). Full bloom in Wenatchee, Wash. in one growing season occurred about April 30$^{th}$.

*Pollination.*—Excellent pollinator. Pollinates 'Golden Delicious'. Pollinated by 'Elstar', 'Gloster 69', 'Golden Delicious', 'Idared', 'James Grieve', 'Melrose', 'Pilot', and 'Sampion', among others.

Fruit:

*Size.*—Medium to large. Three typical fruit grown in Wenatchee, Wash. during one growing season averaged 175 grams, had a cross-sectional dimension in the axial direction averaging 69 mm, and a cross-sectional dimension in the transverse direction averaging 76 mm. Fruit size will vary with the growing season and the extent to which the tree is thinned.

*Shape.*—Conical.

*Cavity.*—Flat.

*Basin.*—Medium to deep. The above-mentioned three apples had a stem basin depth averaging 20 mm.

*Stem.*—Long. The above mentioned three apples had an average stem length of 41 mm. Stem color of these apples was like R.H.S. 172B.

*Calyx.*—Closed.

*Locules (carpels).*—Medium.

*Quality.*—Excellent. Flavor good, sugar-acid balance excellent.

*Texture of Flesh.*—Firm to juicy. Color of flesh, typically a creamy white, like R.H.S. 158A. Pressure 19 pounds typical, soluble solids 14–15 brix typical.

*Use.*—Suitable as dessert apple from November to May in Germany.

*Storage.*—Keeps well in both common cold storage (until April-May) and in controlled atmosphere (until June). Less storage loss than 'Golden Delicious'.

*Yield.*—Very productive (about 120 percent of 'Golden Delicious'). Bears regularly every year (no alternate bearing). Precocious, bearing on one-year-old shoots. Does well on 'M 26' and 'M 9' rootstocks.

Figure 3:
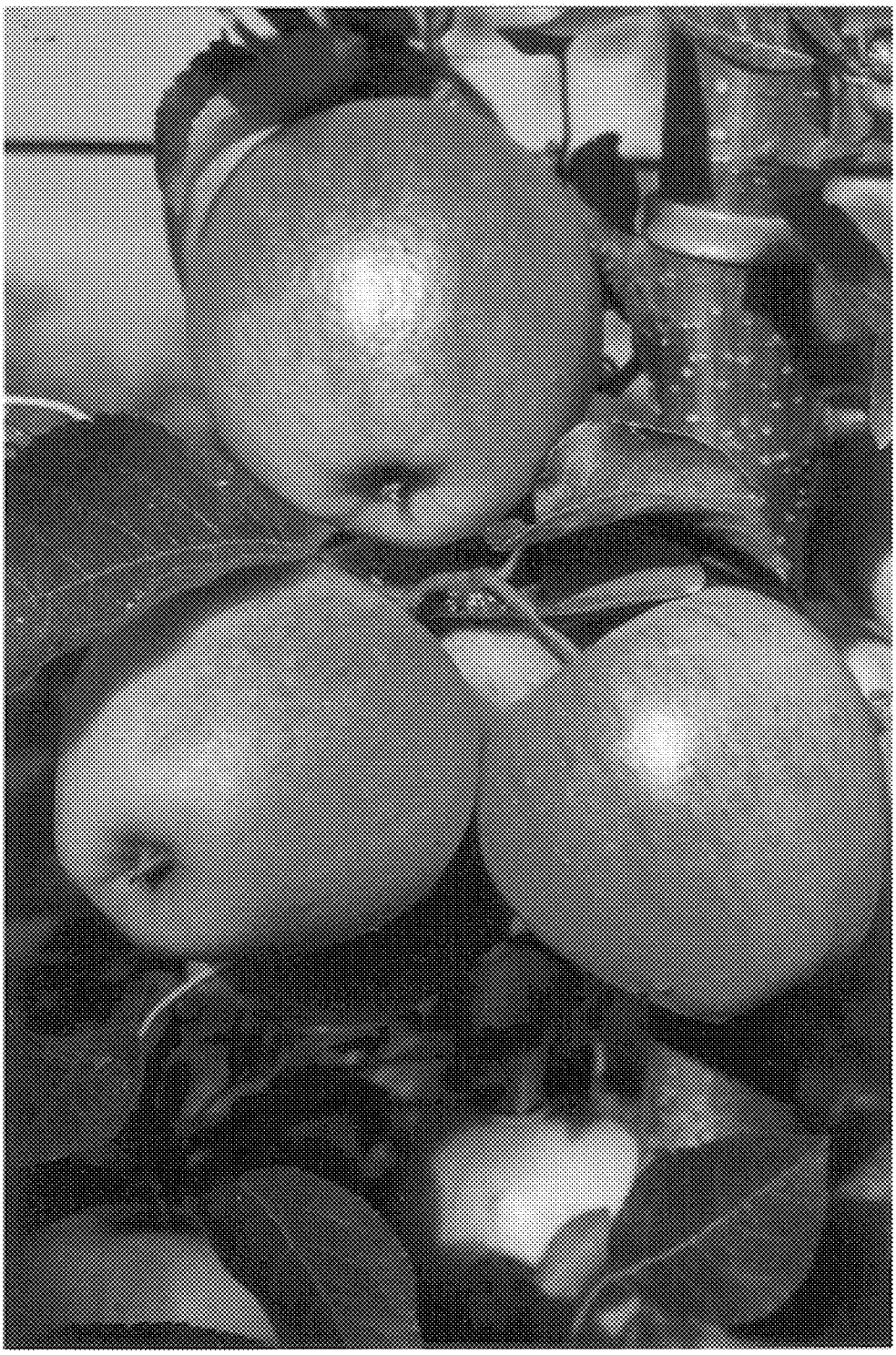
FIG. 3 is a close-up view of fruit and leaves of the variety showing the yellow under color of the fruit.
Figure 4:
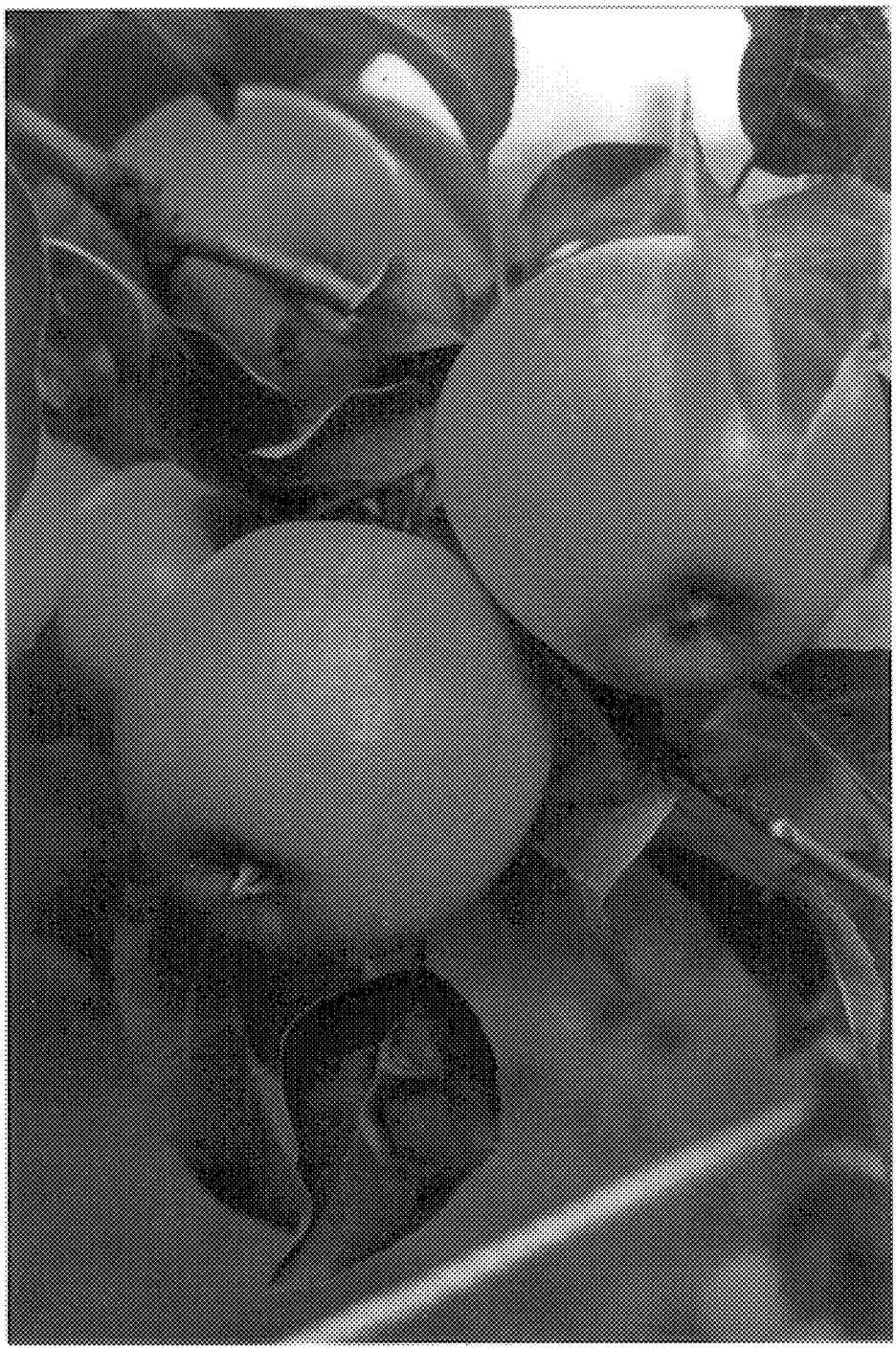
FIG. 4 is a close-up view of fruit and leaves of the variety showing fruit that have a red over color that covers substantially the entire fruit surface.

*Skin.*—Color: Under color: yellow. Varies with growing conditions, like R.H.S. 13B in one observation of fruit at full maturity. Over color: red to vermillion (40–100%; see FIGS. 3 and 4). Varies with growing conditions, like R.H.S. 33A in one observation of fruit at full maturity. Color markings: dark red stripes. Overall: Very attractive bright red to red-orange. Better coloration than 'Golden Delicious'. Lenticels: Small to very small. Color of lenticels: Brown to dark brown. Core: Bundle area: Medium. Core lines: Slight. Calyx-tube: Narrow. Seeds: Number in one cell: 2 (to 3). Length: Long to very long. Breadth: Small. Color: Brown (similar to R.H.S. 200D), darkens toward black (similar to R.H.S. 202A) as fruit ripens.

Ploidy: Diploid with good viable pollen.

Cold resistance: Withstands winter and spring frosts.

Resistance to insects and disease: Only weakly susceptible to scab and fireblight.

I claim:

1. A new and distinct variety of apple tree substantially as herein shown and described.

* * * * *